United States Patent [19]

Conzola et al.

[11] Patent Number: 5,185,638

[45] Date of Patent: Feb. 9, 1993

[54] COMPUTER CONTROLLED, MULTIPLE ANGLE ILLUMINATION SYSTEM

[75] Inventors: Vincent C. Conzola, Endwell; Norman E. Rittenhouse; Jeffrey M. Solomon, both of Endicott, all of N.Y.; Thomas J. Toomey, Denver, Colo.; Peter J. Yablonsky, Apalachin, N.Y.

[73] Assignee: International Business Machines Corporation, Armonk, N.Y.

[21] Appl. No.: 691,941

[22] Filed: Apr. 26, 1991

[51] Int. Cl.⁵ .................. G01N 21/88; G01N 21/47; F21V 8/00; F21V 33/00
[52] U.S. Cl. .................. 356/237; 250/227.29; 356/446; 356/340; 362/32; 362/33
[58] Field of Search ............ 356/237, 446, 340, 250; 362/32, 33; 250/227.29, 227.3

[56] References Cited

U.S. PATENT DOCUMENTS

| | | | |
|---|---|---|---|
| 4,498,778 | 2/1985 | White | 356/376 |
| 4,570,180 | 2/1986 | Baier et al. | 358/106 |
| 4,650,333 | 3/1987 | Crabb et al. | 356/376 |
| 4,677,531 | 6/1987 | Szeles | 362/32 |
| 4,754,329 | 6/1988 | Lindsay et al. | 358/139 |
| 4,758,782 | 7/1988 | Kobayashi | 324/23 |
| 4,794,647 | 12/1988 | Forgues et al. | 382/8 |
| 4,799,175 | 1/1989 | Sano et al. | 364/552 |
| 4,811,410 | 3/1989 | Amir et al. | 382/8 |
| 4,878,114 | 10/1989 | Huynh et al. | 358/106 |
| 4,887,190 | 12/1989 | Sadamune et al. | 362/32 |
| 4,893,223 | 1/1990 | Arnold | 356/237 X |
| 4,893,932 | 1/1990 | Knollenberg | 356/369 |
| 5,038,258 | 8/1991 | Koch et al. | 356/237 X |
| 5,087,822 | 2/1992 | Fairlie et al. | 356/446 X |

Primary Examiner—Vincent P. McGraw
Attorney, Agent, or Firm—Richard M. Goldman; Judith D. Olsen

[57] ABSTRACT

The illumination system as a part of an optical inspection system, the total inspection system itself, and the method of illuminating and inspecting a workpiece. The illumination system is computer controlled as to a level of intensity and adjustable as to angle of incidence. The illumination system includes illumination control electronics, a quad quartz halogen lamp array light source, a fiber optic line converter and an illumination collection system, having a collimator lens array and a focusing/field coverage lens. As a result of the present invention, determinations of false defects on the PCB are minimized. Human contact with the PCB is also minimized and the rate of inspections performable is increased.

4 Claims, 6 Drawing Sheets

COMPUTER CONTROLLED, MULTIPLE ANGLE ILLUMINATION SYSTEM

BACKGROUND OF THE INVENTION

1. Field of the Invention

This invention relates to a flexible and automated optical inspection system (AOI) of focussed multiple angle illumination and reflection.

More particularly, this invention relates to an illumination system used in surface analyzers for printed circuit boards (PCBs). The invention employs automated multiple angle illumination and reflection for the analysis of surface contrasts on PCBs and to detect variations from a predetermined norm. The system and method of the invention is also potentially useful in the photocopier, microscopy and facsimile arts and indeed in other arts wherein optically characterizing contrasts of images on an object is important.

2. Background Art

The optical section of a typical AOI system comprises three main sections: imaging lens; line scan camera/camera controller; illumination system. The line scan camera includes a linear array of photodetectors known as pixels. The pixels store energy corresponding to the light intensity scattered by the object and collected by the imaging lens.

The object scattering pattern, of course, varies with the material and the processing conditions. Likewise the defect set varies with the manufacturing process and the circuit board performance specification. To achieve consistent, reliable results, the scattered light variation must be compensated by adjusting the illumination incidence angle, the illumination intensity, or a combination of incidence angle and intensity.

During the inspection process, the circuit board travels at constant velocity perpendicular to the line scan camera. An image within the width of the camera scan and the length of the circuit board, is collected by the line scan camera. The optical system is translated the width of the camera scan and another sweep of the board is taken. This process is repeated until the image of the entire board is acquired.

Optical surface analysis systems are described in the art. U.S. Pat. No. 4,498,778 issued Feb. 12, 1985 to White describes a system for locating points, as opposed to defects, on a workpiece. The spatial coordinates of the workpiece are determined in a system that includes illumination by a laser at a single, constant and known angle of incidence, the reflection being viewed also at a single angle.

U.S. Pat. No. 4,570,180 issued Feb. 11, 1986 to Baier et al. describes a meander scanning method comprising two steps, the first in which a digitized, stored image is scanned for edges or lines (transitions) and marked. In the second step the unmarked regions are scanned for permissible gray ares. Illumination is not discussed.

U.S. Pat. No. 4,650,333 issued Mar. 17, 1987 to Crabb et al. describes the detection of holes and nodules using single laser incidence and reflection, at a constant angle.

U.S. Pat. No. 4,754,329 issued Jun. 28, 1988 to Lindsay et al. describes the focusing and calibrating of a display screen rather than the illumination of the workpiece.

U.S. Pat. No. 4,758,782 issued Jul. 19, 1988 to Kobayashi describes improvements to the analysis of data obtained by combining feature extraction and mutual comparison methods, concentrating on the computer function and measuring electronics rather than the illumination.

U.S. Pat. No. 4,794,647 issued Dec. 27, 1988 to Forgues et al. describes the simultaneous dimensional verification and pattern recognition used in a probability weighing method of detecting flaws. The illumination is described as emanating from one light source above and a second light source below the workpiece, and one or more cameras above.

U.S. Pat. No. 4,799,175 issued Jan. 17, 1989 describes the table carriage and data manipulation systems after image acquisition rather than the illumination step, the problem addressed being problems in consistent workpiece alignment.

U.S. Pat. No. 4,811,410 issued Mar. 7, 1989 to Amir et al. describes an inspection of electronic devices of the kind mounted on PCBs. Non-uniformity of illumination is compensated for by weighting the threshold value of each pixel rather than by varying the illumination parameters.

U.S. Pat. No. 4,878,114 issued Oct. 31, 1981 to Huynh et al. describes a method of measuring the roughness of the surface of paper or of the finish of a machined part using light incident at an optimal grazing angle and its reflection, preferably through microscope optics, to a video camera.

U.S. Pat. No. 4,893,932 issued Jan. 16, 1990 to Knollenberg describes a method of surface analysis using the split beam of light reflected from two laser beams.

However, nowhere in the art is the AOI system and method of the present invention described, nor is, in particular, the illumination part of the system and method of the present invention.

Various systems are known in the art for determining the contour of an object by viewing the object at an angle from an illuminating beam, and comparing the object with a stored standard. Other systems provide an unacceptably high number of false defect calls due to trivial surface features such as stains and minor scratches.

The present invention provides a means of reducing the object surface variations and selectively highlighting particular defect(s) on circuit boards. The level of intensity of illumination is controlled. The invention provides a larger range of illumination angles and a higher level of irradiance than previous systems. The larger range of illumination angles minimizes the number of false defect calls resulting from spurious surface damage such as stains and minor scratches. Prior knowledge of the optical properties of an ideal of the particular circuit board, the reflectivity and direction of the defect scattering patterns, and the defect sensitivity level desired is used to predetermine the norm and to choose incidence angles at which to set the illumination intensity. Initial calibration only is required for a given workpiece. The calibration for a specific PCB configuration is stored in the computer. Because of the degree of automation in the present system, the number of instances in which direct human intervention is required is kept to a minimum. As a result, the potential for error introduced by direct human intervention and the reduction in throughput which is caused by dependency on direct human intervention in the inspection process is avoided.

SUMMARY OF THE INVENTION

Accordingly, it is an object of the invention to provide the illumination for a noncontact automated optical inspection system for analyzing surfaces having features of contrasting reflectivity.

It is a further object of the invention to provide the noncontact automated optical inspection system of which the illumination means of the present invention is a critical element.

It is a further object of the invention to reduce the number of false defect readings in the inspection step of the manufacturing process for printed circuit boards.

Still another object of the invention is to provide a rapid, programmable system and method for illuminating PCB surface features. The system has been used to examine PCB surfaces having features as small as two mils wide, but is by no means limited to that dimensional region. The principles of the invention are unlimited by dimension.

The foregoing and other objects and advantages are accomplished in the present invention by means of an illumination system within an automated optical inspection system for the inspection of the surface of a printed circuit board or other high contrast workpiece comprising multiple sources of light for impinging incident to the workpiece surface, illumination control electronics for maintaining constant intensity of each of the multiple light sources, multiple fiber optic line converter for coupling the light from the multiple sources into a fiber optic bundle, and a multiple lens light collection system and camera for collecting light reflected from the workpiece surface.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following description taken in conjunction with the accompanying drawing figures in which:

DESCRIPTION OF THE PREFERRED EMBODIMENTS

Figure 1:
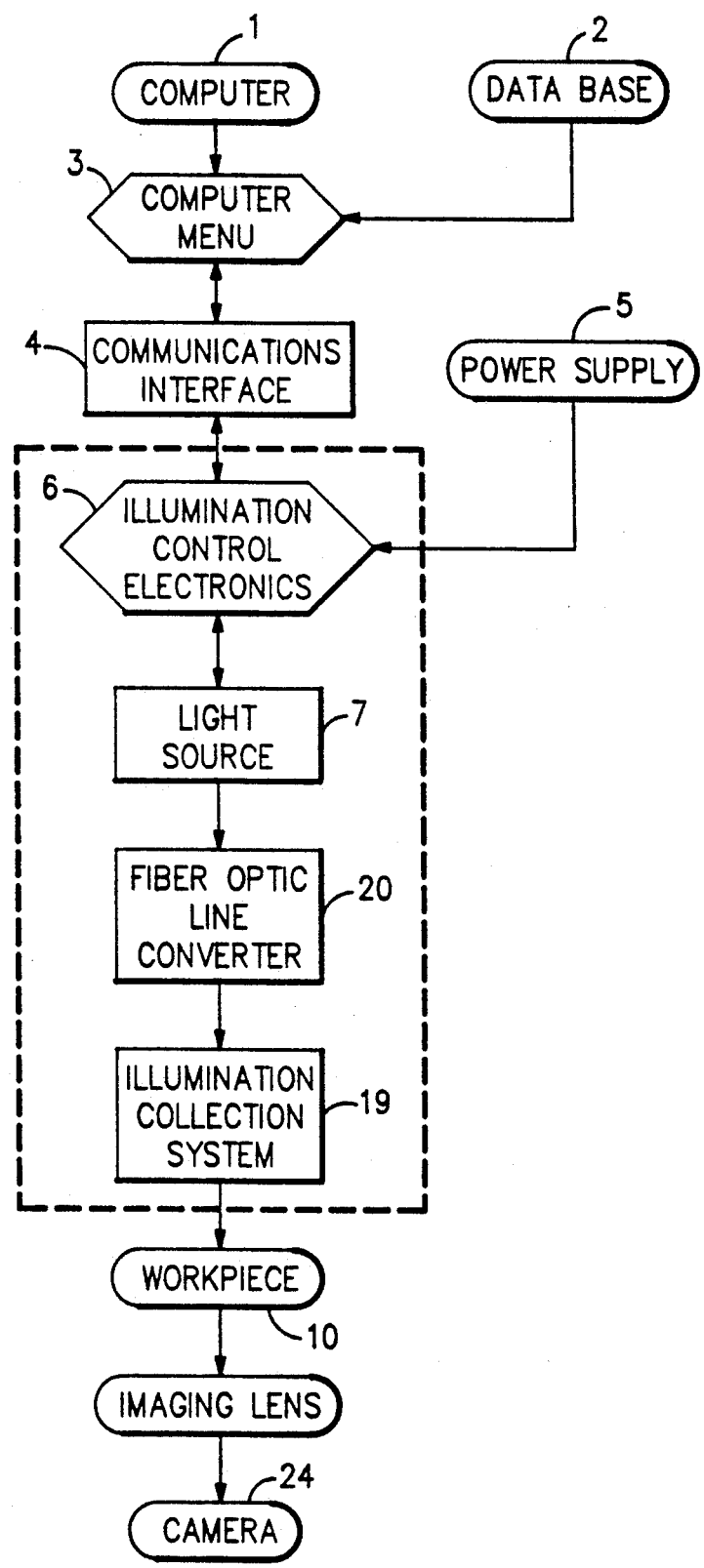
FIG. 1 is a flow chart representation of a computer controlled, multiple angle illumination system in accordance with the present invention.

The computer controlled multiple angle illumination system of the present invention, which is a part of an AOI system, contains four sections: illumination control electronics, light source, fiber optic line converter and illumination collection system.

Each section of the system will be described individually below.

Illumination Control Electronics

Determined by computer input, the illumination control electronics assign discrete voltages to each light source. Energy from a corresponding fiber optic line is directed toward the circuit board surface via the (illumination) collection system. In this manner, each light source corresponds to a separate incident angle of illumination.

The illumination intensity setting for each light source is entered at the computer menu user interface or recalled from the data base. For each light source, a value representing the voltage to be applied to it is sent from the computer to the illumination control electronics via a standard communications interface. The illumination control electronics consists of several identical and independent circuit channels, one channel for each light source in the system. Using the value sent by the computer as an input, each circuit channel regulates the output received from a constant voltage DC power supply. The regulated output from each channel powers the light source corresponding to that channel. By varying the input value from the computer within a specified range, the regulated output voltage can be made to vary between 0 volts and the maximum allowable voltage for the light source.

Since each circuit channel operates independently from the others, all of the channels can be paralleled and driven from a single power supply. In this way, a single constant voltage DC power supply is made to operate as multiple, variable supplies. The number of circuit channels which can be paralleled is limited only by the maximum output current of the power supply.

In addition to providing power to the light sources, the illumination control electronics also measure the output current to each light source and feed it back to the computer as a means of monitoring lamp decay. The computer also controls the angle of illumination.

Light Source

The light source consists of a plurality of lamps, one lamp for each line of the fiber optic line converter. The plurality of lamps is packaged within an elliptical reflector such that the lamp filament is located at the focus of the ellipse. The elliptical reflector collects and focuses the lamp energy to the input face of the fiber optic bundle. This position is known as the light source focus position. The lamp spectrum is filtered by a heat reflecting mirror, eliminating infrared energy (700 nm) from reaching both the circuit board and the charge-coupled device (CCD) line scan camera.

Fiber Optic Line Converter

The fiber optic line converter contains a plurality of discrete glass fiber optic bundles. Each bundle has a circular input face and a rectangular slit output face. The fiber optic lines are arranged in a mechanical housing such that the distance between the centers of adjacent lines is separated by a distance corresponding to the angle of incidence. Each circular input bundle face is placed at a light source lamp focus position, coupling the lamp irradiance into the fiber bundle. The fiber positions in the input and output faces are randomized, preventing a direct correlation between the intensity distribution at the fiber optic input and the output faces. The fiber randomization thereby produces a uniform output from a non-uniform input.

Each fiber within the bundle acts as an individual point source. The optical axis of each fiber is aligned perpendicular to the mechanical housing output face.

Illumination Collection System

The illumination collection system is comprised of two sections: collimator lens array and the focusing/field coverage lens. The collimator lens array contains a plurality of discrete collimators, one collimator to each fiber slit. The collimator lenses are centered with respect to the fiber optic slit centerline.

Figure 10:
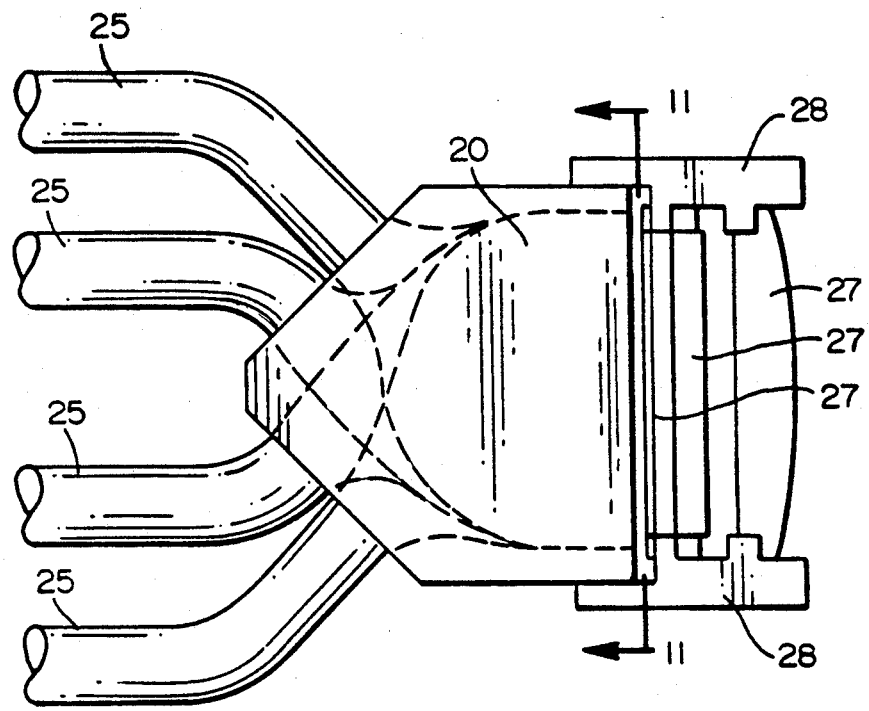
FIGS. 10 & 12 are a plan and a side view respectively of an optic line converter.

The collimator contains a plurality of cylindrical lenses (each of which has curvature in only one axis). The axis having curvature is aligned perpendicular to the fiber slit length. Having a plurality of lenses in the collimator provides additional degrees of freedom for aberration control. For example, having two lenses in the collimator provides six degrees of freedom—two air space thicknesses and four curvatures. The individual lens element curvatures are bent such that the center ray of the extreme off axis light bundle (chief ray) crosses the optical axis at the last surface of the collimator (aperture stop plane) as seen in FIG. 10. The aperture stop placement minimizes the required clear aperture. If the aperture stop were placed closer to the fiber plane, then rays from the off-axis fibers would diverge beyond the lens clear aperture.

The focusing/field coverage lens performs two main functions: it brings the light from the individual bundles to a common focus, and directs the light from the fiber slit ends toward the imaging lens aperture stop. The focusing/field coverage lens has two cylindrical surfaces, one surface perpendicular to fiber slit length (tangential cylinder), and the other surface parallel to the fiber slit length (sagittal cylinder). The tangential cylinder focuses the light bundle from each slit/collimator combination to a common focus. The sagittal cylinder bends the chief ray from each individual fiber to the center of the imaging lens entrance pupil.

Referring now to the drawings and particularly to FIG. 1 thereof, the computer 1 consists of an IBM PC/AT processor or the equivalent configured with a hard disk drive, color monitor, and IEEE 488 interface board. The data base 2 is stored on the hard disk and contains illumination intensity settings for each unique part number of the workpiece 10 such as a circuit board, to be optically tested. The information for each part number is stored as a series of voltage values; one value for each individual lamp of the light source 7 in the system. The computer menu 3 user interface allows the system operator to display the illumination intensity settings for the light sources 7 and quickly modify them for optimal image contrast and defect detection sensitivity. The operator can see the effect of changing the voltage value for each light source 7 by viewing the analog video output from the CCD camera 24 on an oscilloscope (not shown). Controlling the light source 7 voltages from the computer 1 allows for rapid recall and setup of the illumination system when switching between part numbers under test or when testing a given part number of circuit board for the first time.

After the illumination intensity settings for the light source 7 have been entered at the computer 1 they are sent via IEEE 488 to a communications interface 4. This interface may be an IOtech Digital 488/80 configured with separate 8-bit input and output ports. The communications interface 4 converts the illumination intensity settings to discrete 8-bit digital signals and sends them from its output ports to the illumination control electronics 6. The illumination control electronics 6 consist of four indentical but independent circuit channels, one channel for each light source 7 in the system.

Figure 2:
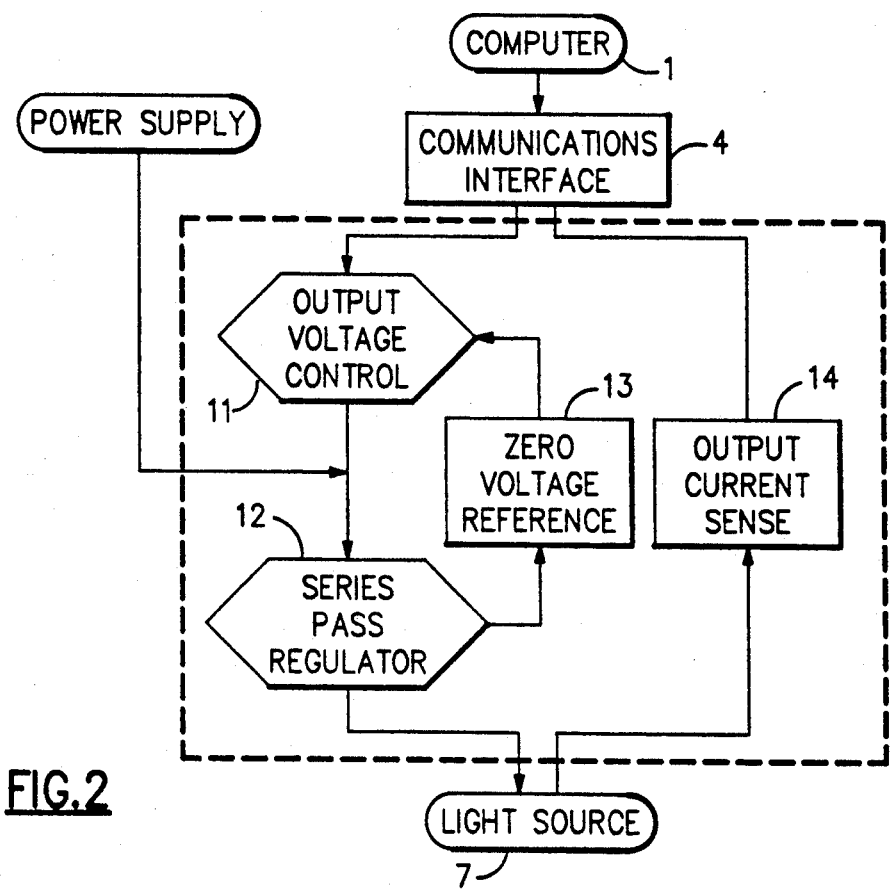
FIG. 2 is a flow chart representation of the illumination control electronics of FIG. 1 with the illumination control electronics within the dotted-line box and the devices with which the illumination control electronics interacts outside the dotted-line box.

FIG. 2 shows a block diagram representation of a single channel including the output voltage control 11, series pass regulator 12, zero voltage reference 13, and output current sense 14 sections. The output voltage control 11 circuitry includes a digital-analog converter (DAC) which converts the illumination intensity setting for that channel's light source 7 from the 8-bit digital representation sent by the communications interface 4 to a scaled (0–10 volt) analog control voltage. The series pass regulator 12 consists of a 200 W NPN power transistor, such as a Motorola MJ802, with a Darlington transistor configuration connected to its base. The collector of the power transistor is connected through a fuse to the output of a 28 volt DC power supply 5 such as a Lambda LFS50-28. The emitter of the power transistor is the output of the circuit channel and supplies the power for the light source 7. As the analog control voltage is increased the current into the base of the power transistor, through the Darlington, increases, forcing the emitter voltage of the power transistor to rise. By properly tuning the output voltage control 11 and zero voltage reference 13 circuits, and feeding the output voltage back, the voltage to the light source 7 can be held stable at a value directly proportional to the analog control voltage and equal to the illumination intensity setting entered at the computer. A 0 to 10 volt swing in the analog control voltage results in a 0 to 24 volt swing in the output voltage to the light source, 24 volts being the maximum allowable voltage for the quartz halogen lamps being used in the light source 7.

The output current sense 14 circuitry measures the output current to the light source 7, digitizes it, and sends it back to the computer 1 through the input port of the communications interface 4. At the computer, the measured output current value is compared to a calculated value based on the illumination intensity setting. Any discrepancy between the two values, above a certain noise level, is due to lamp decay. By monitoring lamp decay, the end of life for each light source can be predicted and the light source replaced proactively.

Figure 3:
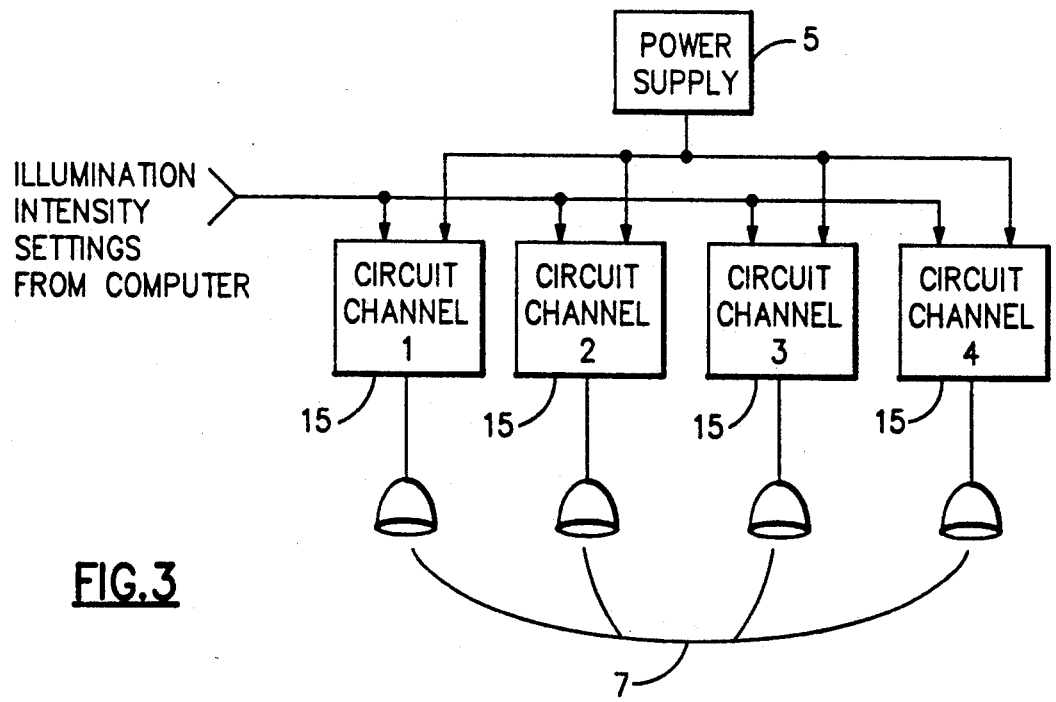
FIG. 3 is a block diagram representation of a power supply driving multiple circuit channels to illuminate an equal number of lamps (the light source of FIGS. 1 and 2) in the illumination control electronics.
Figure 4:
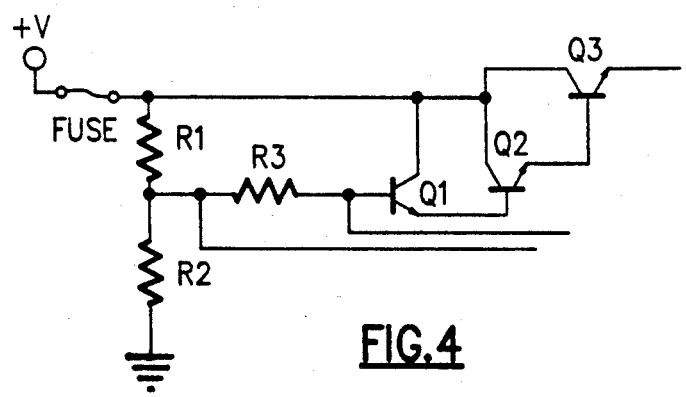
FIG. 4 is a diagram of the series pass regulator shown in FIG. 2.

FIG. 3 shows how a single 28 volt DC power supply 5 is used to drive all four circuit channels 15 of the illumination control electronics 6. Since the circuit channels 15 are independent of each other, there is no loading effect between them. As a result the output of each circuit channel 15 acts as a programmable, variable output (0–24 volts), power supply, whose output voltage is equal to the value sent from the computer 1 through the communications interface 4. Using the illumination control electronics 6 shown in FIG. 1, in this way offers a great efficiency advantage over having to use separate programmable power supplies to drive each light source 7. This power configuration is also applicable outside the immediate scope of the present invention. The output voltage of the power supply used is not limited to 28 volts nor are the load voltages limited to 0-24 volts. Also, the type of load is not limited to quartz halogen lamps nor is the number of loads limited to four. The only limitations to the configuration are the maximum output current of the power supply and an inherent 2.0-3.0 voltage drop between the power supply output and the loads.

The components of FIGS. 4, 5, 6 and 7 interact as follows to create one channel of illumination control electronics.

An 8 bit lamp address bus (not shown) from the communications interface 4 shown in FIG. 1 sends illumination intensity values to an address decode PAL (not shown). The address decode PAL selects the circuit channel to which the illumination intensity value on the data bus is sent. The DAC shown at the input of FIG. 6, which represents the Output Voltage Control circuit, converts the digital value on the data bus to a 0-10 volt analog control voltage. (an 8 bit intensity data bus from the communications interface 4 is shown only as an arrow to the left of the DAC in FIG. 6.) A percentage of the control voltage, based on the values of R4 and R5, is applied to the non-inverting input of an analog voltage comparator (U3). (C1 is not described.) If the voltage on the non-inverting input is less than the voltage on the inverting input, then the open-collector output transistor of the comparator turns on and draws current away from the base of Q1 in the FIG. 4 Series Pass Regulator. Decreasing the current through Q1 causes the current through Q2 to drop, which in turn lowers the base current into Q3. Decreasing Q3's base current causes its collector-emitter voltage to increase, thus lowering the output voltage to the lamp (R1, R2 and R3 are self-evident and are not described). Feeding a percentage based on P1 of the FIG. 6 output voltage back to the inverting input of U3 keeps the output stable. If the voltage on the non-inverting input of U3 is greater than the voltage on the inverting input, then U3 shuts off, more current goes through the Series Pass Regulator of FIG. 4, and the output voltage increases.

Figure 7:
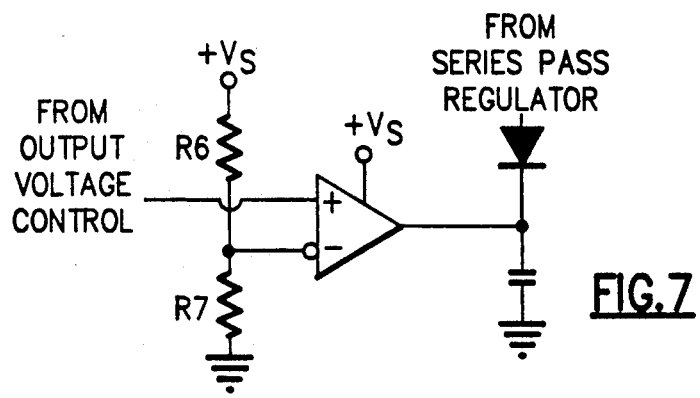
FIG. 7 is a diagram of the zero voltage reference shown in FIG. 2.

The Zero Voltage Reference circuit, FIG. 7, is important only when the analog control voltage is very small. When this control voltage, which is applied to the non-inverting input of U4, is below a certain threshold voltage, determined by R6 and R7 and applied to the inverting input of U4, the comparator turns on and the current which normally flows into the base of Q1 in FIG. 4 instead flows through CR1 to ground. (C2 is not described.) This forces Q1, Q2 and Q3 to shut off completely and causes the output voltage to the lamps to go to 0 volts.

Figure 5:
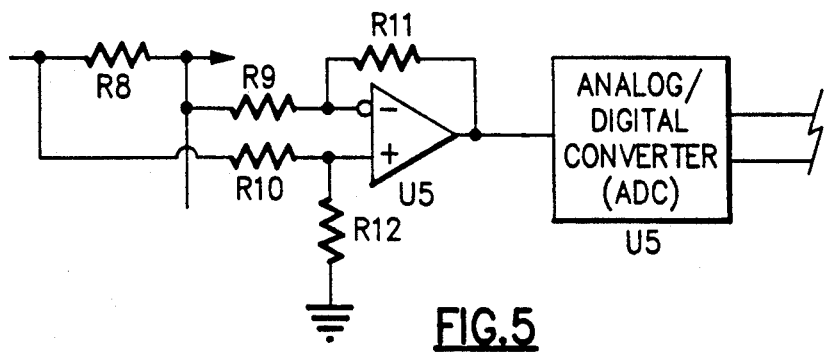
FIG. 5 is a diagram of the output current sense, shown in FIG. 2.
Figure 6:
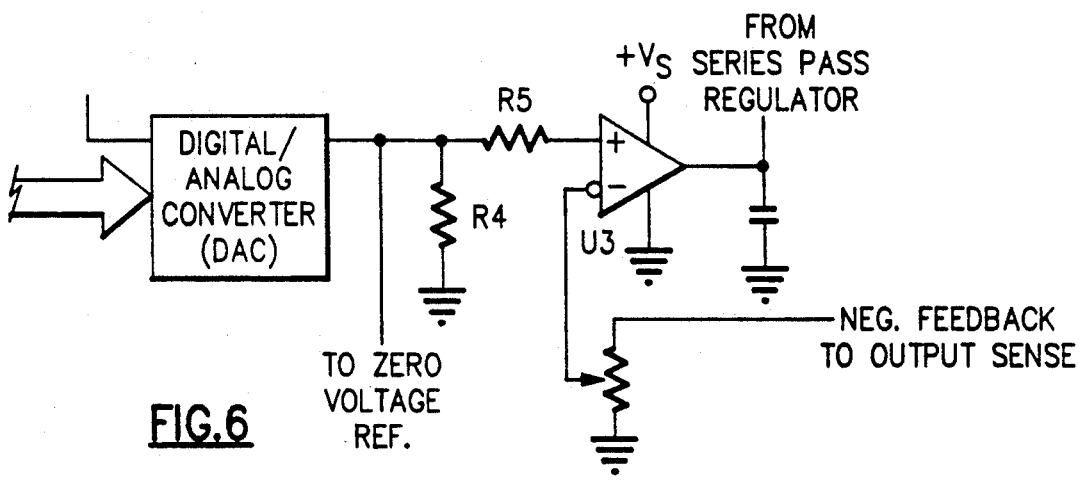
FIG. 6 is a diagram of the output voltage control shown in FIG. 2.

The Output Current Sense circuit, FIG. 5, measures the voltage on either side of power resistor R8. These voltages are then applied to the inputs of a differential amplifier, U5, which outputs the difference voltage across R8, referenced to ground. This voltage is sent to the ADC, U6, digitized and sent to the communications interface. The difference voltage and the value of R8 are used to calculate the output current through R8 to the lamp. (R9, 10 and 11 are evident and are not described.)

Figures 8A, 8B, 8C:
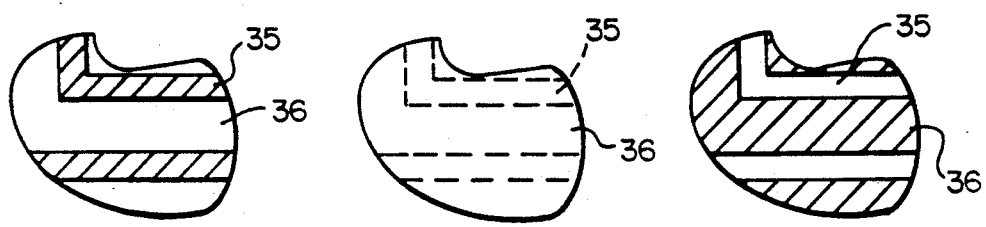
FIGS. 8a, b and c illustrate the types of image contrasts obtainable at several angles of reflectance from an area of a PCB which is illuminated at a fixed angle of incidence.
Figure 8:
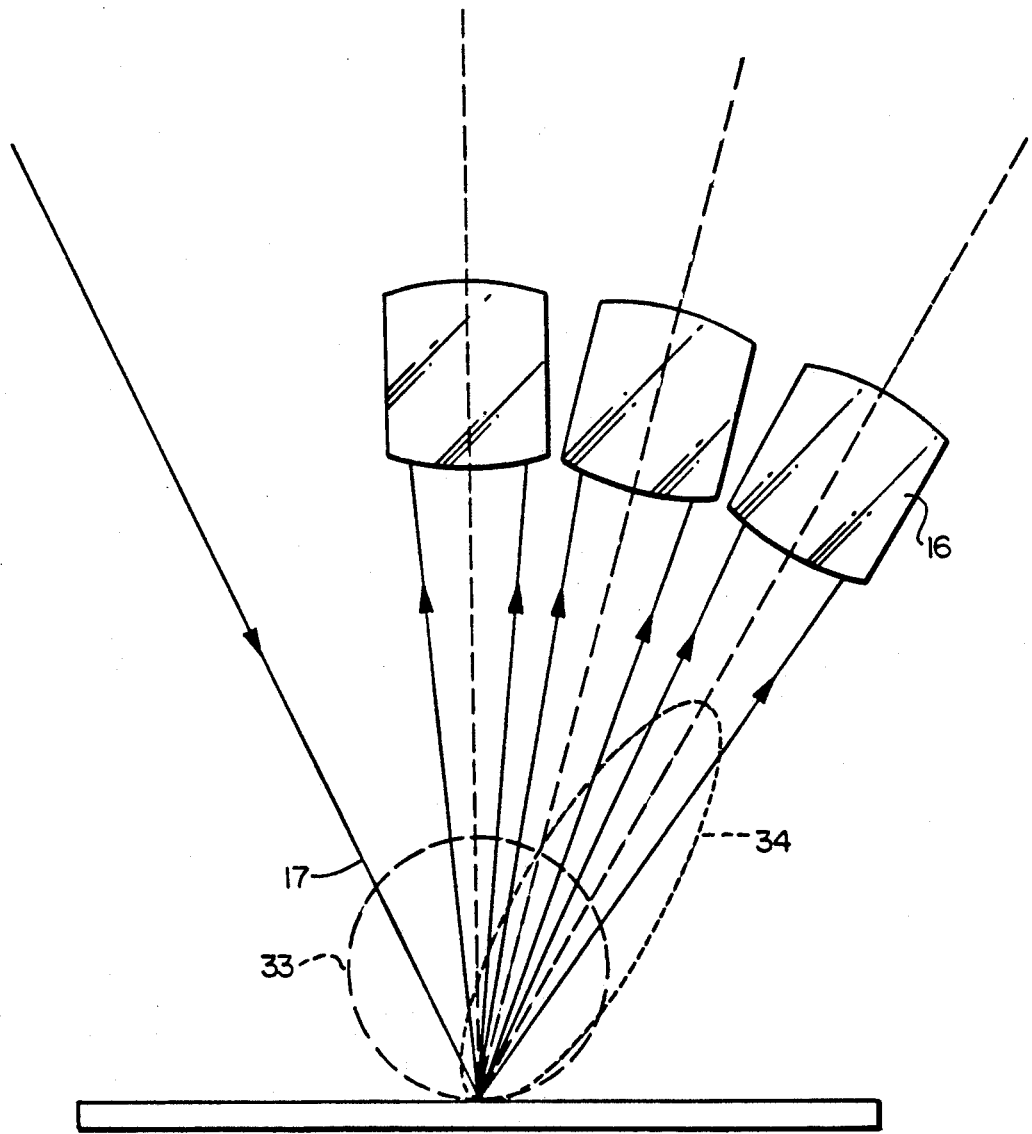

FIGS. 8a, b and c illustrate what is meant by specular 34 and diffuse 33 lighting by showing reflections off copper and dielectric laminant. In the diagram, it can be seen that by varying the imaging lens 16 position, or equivalently by varying the illumination angle of incidence 17, we can improve the imaging contrast of copper to laminate 18. Note the ability to image copper 35 over laminate 36 increases from a to b to c, which show progressive image contrast. Although the present invention is directed to multiple angle illumination, only one angle of incidence is shown as representative in FIG. 8 because of the complexity of showing the reflections for each angle of incidence.

Figure 9:
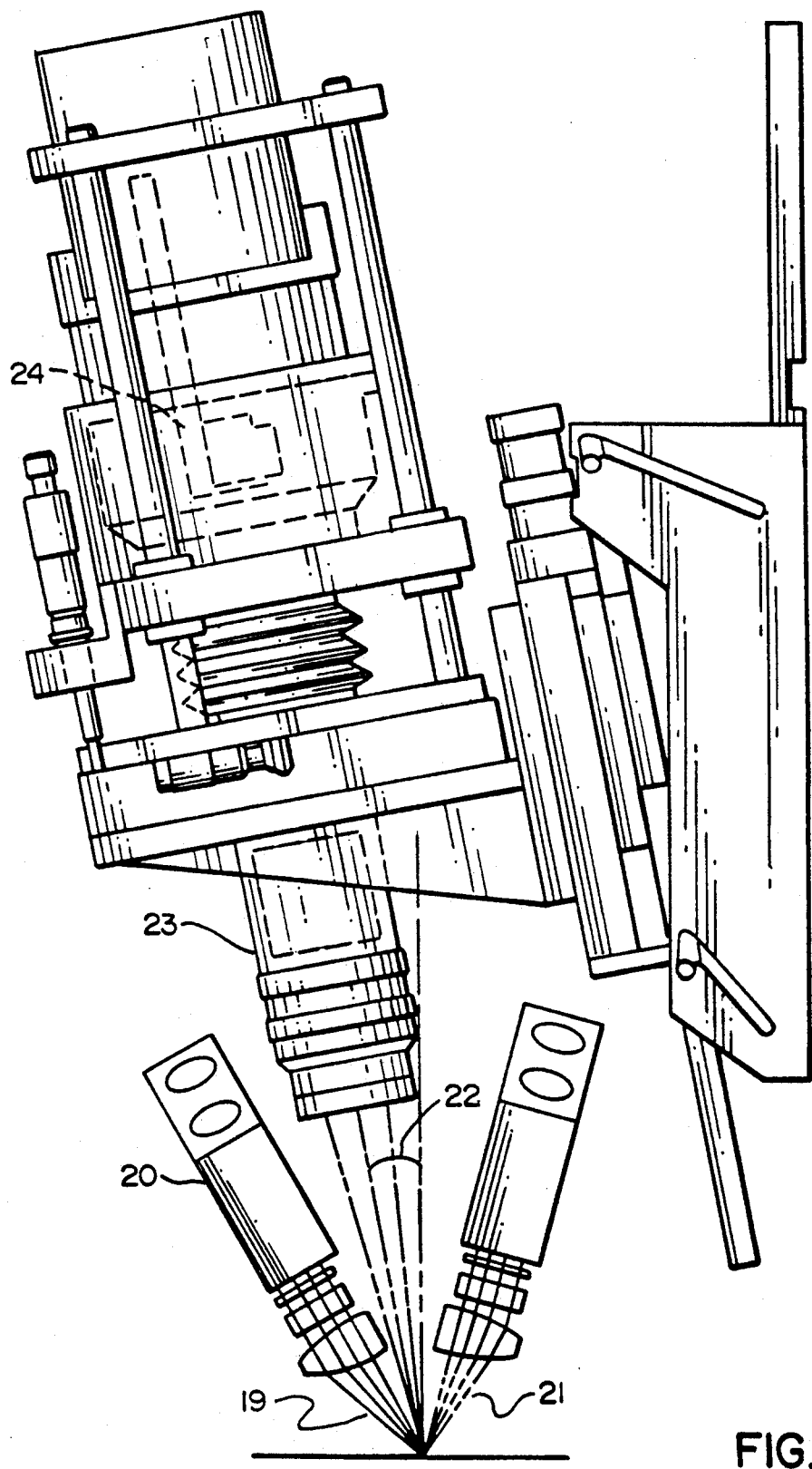
FIG. 9 is a side view of the fiber optic line converter and the illumination collection system sections used in FIG. 1.

FIG. 9 illustrates the placement of the optical section of the invention (minus the light source and bundles) on the mechanical head within the context of an automated optical inspection machine. The three main sections of a typical AOI system are included: Imaging lens; line-scan camera/camera controller; illumination system. The illumination collection system 19 is shown without its mechanical bracketry. A quad fiber optic line converter 20 provides four discrete fiber optic rectangular sources of illumination. Each converter contains four fiber bundles 25 shown in FIG. 10. The fiber bundle has a 16mm diameter input face, is 55 inches long and has a 2 mm by 75 mm rectangular output face. Illumination to each bundle is provided by a light source 7 consisting of a 24 Volt 200 Watt quartz halogen lamp. The lamp is packaged with an elliptical reflector such that the emitted light is focused to the input face of the bundle. The four fiber optic lines (rectangles) are arranged in a mechanical housing such that the center line of each 2 mm wide line is separated by 6.35 mm. The angular placement of this mechanical housing is accomplished by an adjustment of a spring loaded pivoting bracket (not shown). This spacing, in conjunction with the angular placement of the two converters, establishes the following eight angles of incident light 21: 10 deg, 42 deg, $-30$ deg, $-42$ deg, $-53$ deg and $-62$ deg. (Due to spherical aberration at the larger degrees of incidence, it may be helpful to remove the greatest angle from each converter.) The angle of acceptance 22 of the imaging lens shown 23 is $-10$ deg. The imaging lens is a 105 mm focal length Nikon "Printing Nikkor", part number 95191. The line scan charge coupled device (CCD) camera 24 is a Fairchild $1 \times 2048$ linear array CCD, part number CCD 143 (camera controller not shown). Filtering the lamp spectrum with a heat absorbing filter (not shown) prevents infrared energy (700 nm) from reaching both the circuit board and the camera.

Figure 11:
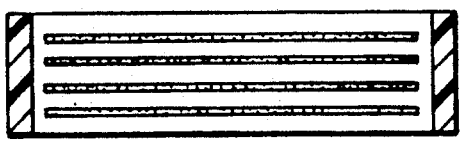
FIG. 11 is an isometric view of an illumination collection system in an assembled unit.

FIG. 10 shows the fiber optic bundles 25, fiber optic line converter (20), illumination collection system 19 and the mechanical bracketry 28 in an assembled unit. An isometric view is given in FIG. 11 in order to show the series of cylindrical lenses cemented together and their placements relative to the quad fiber optic line converter. Each cemented lens corresponds to a rectangular fiber optic light source. As discussed above, the illumination collection system can be split into two sections: collimator lens array and the focusing lens.

Figure 12:
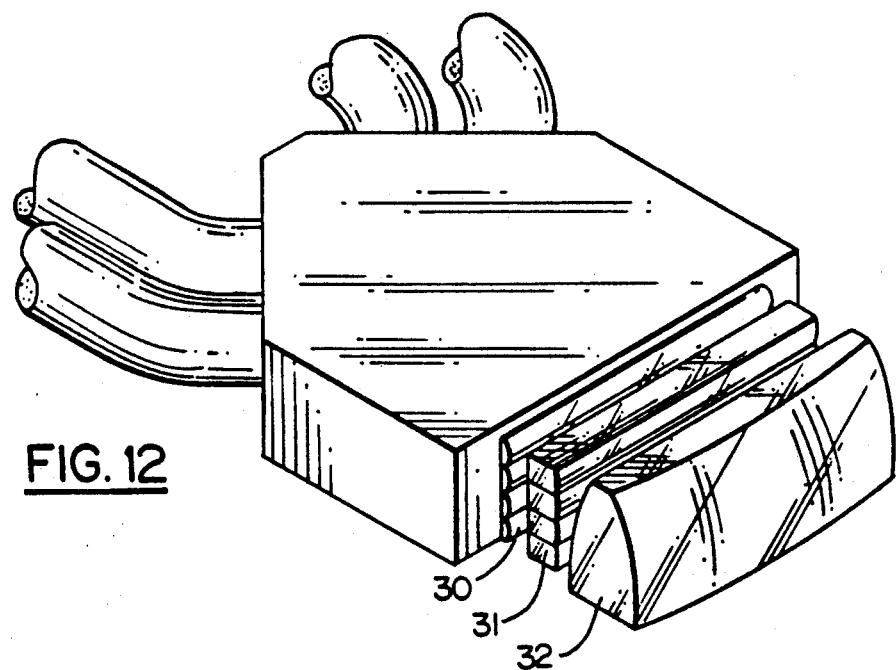

As shown in FIG. 12, the collimator lens array contains two cylindrical lenses 30, 31, and has a focal length of 9.33 mm. The first lens of the collimator 30 is a meniscus lens. The individual fiber optic bundles assembled to form a rectangular line are 50 um in diameter and have a 0.55 numerical aperture corresponding to a 66 degree solid angle. Eighty percent of the output energy is contained within a thirty degree solid angle. The collimator focal length is chosen such that the thirty degree field is collected without vignetting by the 6.35 mm lens clear aperture. To achieve uniform irradiance across the image plane of the lens system, it is suggested to remove the sagittal curvature from the focusing lens 32.

It is understood that the invention may be embodied in modifications of the present invention without departing from the spirit or central characteristics thereof. The aforementioned examples and embodiments are therefore to be considered in all respects as illustrative rather than restrictive, and the invention is not intended to be limited to the details given herein.

What is claimed is:

1. An automated optical inspection system comprising:
   an illumination system which includes multiple sources of light for impinging at multiple angles incident to the surface of a workpiece;
   illumination control electronics for maintaining constant intensity of each of the multiple light sources;
   multiple fiber optic line converter for coupling the light from each of the multiple sources into a fiber optic bundle; and
   a multiple lens light collection system for focusing light on the surface of a workpiece; and
   means for calculating the digital percent voltage value of each lamp in the illumination system;
   means for converting the digital percent-voltage values for each lamp of the illumination system to an analog control voltage;
   means for supplying a constant DC voltage to each lamp of the illumination system as a variable voltage supply; and
   means for using the analog control voltages to control the constant voltage power supply.

2. An illumination system for the inspection of the surface of a workpiece, comprising:
   a. multiple sources of light for impinging at multiple angles incident to the surface of a workpiece;
   b. illumination control electronics for maintaining constant intensity of each of the multiple light sources, said illumination control electronics comprising:
      i. a fused power supply input for limiting the series pass regulator input current;
      ii. a series pass regulator, the output for which powers the system light sources;
      iii. an output voltage control and a zero voltage reference for driving an output power transistor in the series pass regulator between cutoff and saturation;
      iv. a computer for controlling the intensity of and setting incidence angles of each lamp and for storing data derived from prior knowledge of optical properties of the workpiece and analyzing lamp decay;
      v. an output current sense for monitoring the decay of each lamp and sending the information to the computer; and
      vi. a means for regulating the output of a single DC power supply to make it operate as multiple variable voltage supplies, one to each lamp of the illumination system;;
   c. multiple fiber optic line converter for coupling the light from each of the multiple sources into a fiber optic bundle; and
   d. a multiple lens light collection system for focusing light on the surface of a workpiece.

3. An illumination system for the inspection of the surface of a workpiece, comprising:
   a. multiple sources of light comprised of a plurality of quartz halogen lamps for impinging at multiple angles incident to the surface of a workpiece;
   b. illumination control electronics for maintaining constant intensity of each of the multiple light sources, said illumination control electronics including:
      i. a computer for calculating the percent lamp voltage from 0V to maximum and sending the result to a digital-to-analog converter by way of a communication interface for controlling and for calculating and storing voltage data representing the intensity of each lamp;
      ii. A digital-to-analog converter for receiving from the computer the digital data representing the calculated intensities and converting the data to a scaled analog control voltage; and
      iii. A constant DC voltage supply for operating each source of light within the scaled analog control voltage range in response to information received from the DAC;
   c. multiple fiber optic line converter for coupling the light from each of the multiple sources into a fiber optic bundle; and
   d. a multiple lens light collection system for focusing light on the surface of a workpiece.

4. An illumination system for the inspection of the surface of a workpiece, comprising:
   a. multiple sources of light comprised of a plurality of quartz halogen lamps for impinging at multiple angles incident to the surface of a workpiece;
   b. illumination control electronics for maintaining constant intensity of each of the multiple light sources, said illumination control electronics including:
      i. a computer for calculating the percent lamp voltage from 0 V to maximum and sending the result to a digital-to-analog converter by way of a communications interface for controlling and for calculating and storing voltage data representing the intensity of each lamp;
      ii. a digital-to-analog converter for receiving from the computer the digital data representing the calculated intensities and converting the data to a scaled analog control voltage range from V=0 to about 10 V; and
      iii. A constant DC voltage supply for operating each source of light within the scaled analog control voltage range in response to information received from the DAC;
   c. multiple fiber optic line converter for coupling the light from each of the multiple sources into a fiber optic bundle; and
   d. a multiple lens light collection system for focusing light on the surface of a workpiece.

* * * * *